United States Patent
Göbbel et al.

(10) Patent No.: US 7,323,579 B2
(45) Date of Patent: Jan. 29, 2008

(54) SEPARATION OF PROPYLENE OXIDE FROM A MIXTURE COMPRISING PROPYLENE OXIDE AND METHANOL

(75) Inventors: Hans-Georg Göbbel, Kallstadt (DE); Henning Schultz, Mannheim (DE); Peter Schultz, Bad Dürkheim (DE); Renate Patrascu, Stade (DE); Malte Schulz, Hollern-Tw. (DE); Meinolf Weidenbach, Drochtersen (DE)

(73) Assignees: BASF Aktiengesellschaft, Ludwigshafen (DE); The Dow Chemical Company Legal Department Intellectual Property Section, Midland, MI (US)

( * ) Notice: Subject to any disclaimer, the term of this patent is extended or adjusted under 35 U.S.C. 154(b) by 173 days.

(21) Appl. No.: 10/884,968

(22) Filed: Jul. 7, 2004

(65) Prior Publication Data

US 2006/0009648 A1    Jan. 12, 2006

(51) Int. Cl.
*C07D 301/32* (2006.01)
*C07D 301/03* (2006.01)
*B01D 3/34* (2006.01)

(52) U.S. Cl. .......... 549/541; 549/538; 203/53; 203/54; 203/57; 203/58

(58) Field of Classification Search ............. 549/541, 549/538; 203/53, 54, 57, 58
See application file for complete search history.

(56) References Cited

U.S. PATENT DOCUMENTS

| 4,140,588 A | * | 2/1979 | Schmidt ............... 203/92 |
| 5,849,938 A | | 12/1998 | Rueter et al. |
| 6,500,311 B1 | | 12/2002 | Sawyer |

FOREIGN PATENT DOCUMENTS

| DE | 118 873 A1 | 3/1976 |
| EP | 0 811 617 A1 | 12/1997 |
| EP | 1 424 332 A1 | 6/2004 |

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

A method of separating propylene oxide from a mixture (M) comprising 5 to 50 percent by weight propylene oxide and 50 to 85 percent by weight methanol, said method comprising (i) introducing said mixture (M) into an extractive distillation column;
(ii) additionally introducing a polar solvent into said extractive distillation column;
(iii) distilling propylene oxide overhead from said extractive distillation column at a bottoms temperature of from 40 to 70° C. and at a pressure of from 300 to 750 mbar.

27 Claims, 3 Drawing Sheets

SEPARATION OF PROPYLENE OXIDE FROM A MIXTURE COMPRISING PROPYLENE OXIDE AND METHANOL

FIELD OF THE INVENTION

The present invention relates to a method of separating propylene oxide from a mixture (M) comprising from 5 to 50 percent by weight propylene oxide and from 50 to 85 percent by weight methanol. This method comprises
(i) introducing said mixture (M) into an extractive distillation column;
(ii) additionally introducing a polar solvent into said extractive distillation column; and
(iii) distilling propylene oxide overhead from said extractive distillation column at a bottoms temperature of from 40 to 70° C. and at a pressure of from 300 to 750 mbar.

According to a preferred embodiment of the present invention, the mixture (M) is formed by a reaction of propene with hydrogen peroxide in methanol as solvent and in the presence of a titanium zeolite fixed-bed catalyst. Therefore, the present invention also provides a method of preparing propylene oxide, wherein said reaction comprises reacting propene with hydrogen peroxide in methanol as solvent and in the presence of a titanium zeolite fixed-bed catalyst. This epoxidation reaction results, either directly or after at least one work-up step, in a mixture (M) which comprises from 5 to 50 percent by weight propylene oxide and from 50 to 85 percent by weight methanol, and the method of the present invention further comprises
(i) introducing said mixture (M) into an extractive distillation column;
(ii) additionally introducing a polar solvent into said extractive distillation column, and
(iii) distilling propylene oxide overhead from said extractive distillation column at a bottoms temperature of from 40 to 70° C. and at a pressure of from 300 to 750 mbar.

BACKGROUND OF THE INVENTION

At atmospheric pressure or superatmospheric pressures, essentially in the range from 1 to 5 bar, propylene oxide and methanol can be separated by distillation only when a distillation column having a very large number of theoretical plates is used and a very high reflux ratio is set at the same time, owing to the entraining azeotrope.

These mixtures comprising propylene oxide and methanol result, e.g., from epoxidation processes where propene is reacted with a hydroperoxide such as hydrogen peroxide in the presence of methanol as solvent.

U.S. Pat. No. 5,849,938 discloses a process where propene is separated from methanol in a crude olefin epoxidation product by means of an extractive distillation wherein a relatively heavy polar solvent having hydroxy groups such as water or propylene glycol is used as the extracting solvent, propylene glycol being particularly preferred. According to this document of the prior art, the distillation column used ordinarily has from 20 to 60 theoretical plates, and the refluxidistillate ratio is generally in the range of from 5 to 15. According to the examples, a typical ratio is 9. Typical bottoms temperatures are in the range of from 90 to 120° C., the pressure under which distillation is carried out being from 0.55 to 3.44 bar. According to the example, a preferred bottom pressure of the distillation column is 2.76 bar and therefore well above standard pressure. As typical propylene oxide fractions, fractions are obtained comprising 300 or 1,500 ppm of methanol. The bottoms fractions obtained according to the examples comprise up to 6,300 ppm of propylene oxide.

U.S. Pat. No. 6,500,311 B1 discloses a process wherein a separation of methanol and propylene oxide takes place. As extracting solvent, a non-polar solvent, namely a C7-C9 hydro-carbon such as n-octane is used.

It is an object of the present invention to provide a method of separating propylene oxide from methanol which, compared to the processes described in the prior art, has an improved energy balance and, additionally, leads to top streams and bottoms streams having a lesser degree of impurity with regard to methanol and propylene oxide, respectively.

It is a further object of the present invention to provide a method of separating propylene oxide from methanol in which a cheap extracting solvent is employed which simultaneously allows for milder distillation conditions than those described in the prior art.

It is still another object of the present invention to provide a method of producing propylene oxide in the course of which propylene oxide is separated from methanol wherein this separation has the above-mentioned advantages thus rendering the method for producing propylene oxide energetically and also with respect to the purity of the distillation fractions advantageous over the prior art.

SUMMARY OF THE INVENTION

The present invention relates to a method of separating propylene oxide from a mixture (M) comprising 5 to 50 percent by weight propylene oxide and 50 to 85 percent by weight methanol, said method comprising
(i) introducing said mixture (M) into an extractive distillation column;
(ii) additionally introducing a polar solvent into said extractive distillation column;
(iii) distilling propylene oxide overhead from said extractive distillation column at a bottoms temperature of from 40 to 70° C. and at a pressure of from 300 to 750 mbar.

The present invention relates to a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation column in an amount of 2 percent by weight of the mixture (M) or less;
(iii) distilling propylene oxide overhead from said extractive distillation column at a bottoms temperature of from 40 to 70° C. and at a pressure of from 300 to 750 mbar.

The present invention relates to a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation;
(iii) distilling propylene oxide overhead from said extractive distillation column at a bottoms temperature of from 40 to 70° C. and at a pressure of from 300 to 750 mbar;

wherein the distillate is partially refluxed into said extractive distillation column and wherein the mass ratio of reflux to distillate is smaller than or equal to 4.

The present invention relates to a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation;
(iii) distilling propylene oxide overhead from said extractive distillation column at a bottoms temperature of from 40 to 70° C. and at a pressure of from 300 to 750 mbar;
(iv) withdrawing a bottoms stream from said extractive distillation column, said bottoms stream comprising 100 ppm propylene oxide or less, and withdrawing a top stream from said extractive distillation column, said top stream comprising 100 ppm methanol or less.

The present invention relates to a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water as vapor at a pressure of not more than 2 bar into said extractive distillation column;
(iii) distilling propylene oxide overhead from said extractive distillation column at a bottoms temperature of from 40 to 70° C. and a pressure of from 300 to 750 mbar.

The present invention relates to a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation column in an amount of 2 percent by weight of the mixture (M) or less;
(iii) distilling propylene oxide overhead from said extractive distillation column at a bottoms temperature of from 40 to 70° C. and a pressure of from 300 to 500 mbar;
(iv) withdrawing a bottoms stream from said extractive distillation column, said bottoms stream comprising 100 ppm propylene oxide or less, and withdrawing a top stream from said extractive distillation column, said top stream comprising 10 ppm methanol or less.

The present invention relates to a method of preparing propylene oxide, said reaction comprising reacting propene with a hydroperoxide in methanol as solvent, said reaction resulting in a mixture (M) comprising 5 to 15 percent by weight propylene oxide, 50 to 85 percent by weight methanol, and 10 to 25 percent by weight water, or resulting in a mixture being worked up to give said mixture (M), said method further comprising
(i) introducing said mixture (M) into an extractive distillation column;
(ii) additionally introducing water as vapor at a pressure of not more than 2 bar into said extractive distillation column in an amount of 0.45 to 1 percent by weight of the mixture (M);
(iii) distilling propylene oxide overhead from said extractive distillation column as top stream at a pressure of from 450 to 500 mbar and a bottoms temperature of from 50 to 60° C.;
(iv) withdrawing a bottoms stream from said extractive distillation column, said bottoms stream comprising 100 ppm propylene oxide or less, and withdrawing a top stream from said extractive distillation column, said top stream comprising 50 ppm methanol or less.

BRIEF DESCRIPTION OF THE DRAWINGS

The accompanying
FIG. 1 provides a diagram showing a preferred embodiment of the present invention,
FIG. 2 provides a diagram showing a process of the prior art,
FIG. 3 provides a diagram showing another process of the prior art.

DETAILED DESCRIPTION OF THE INVENTION

Figure 1:
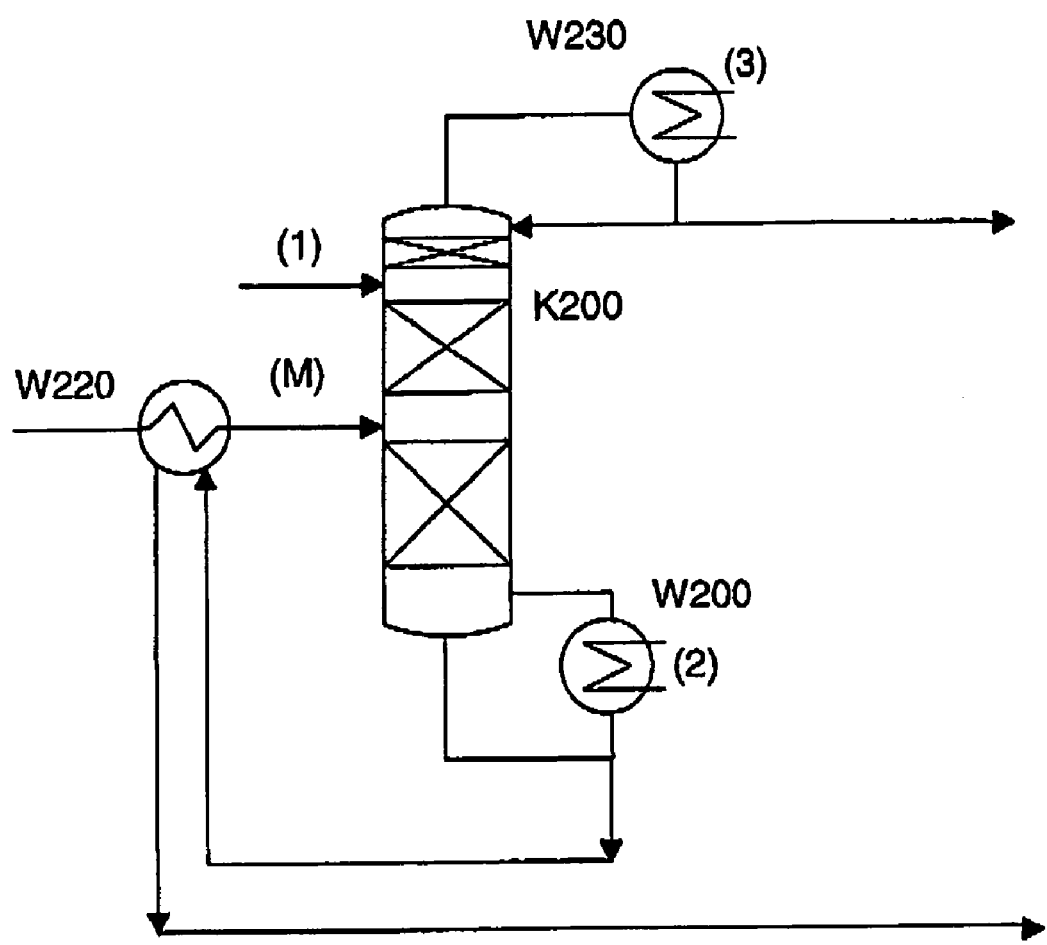

According to the present invention, propylene oxide is separated from a mixture (M) which comprises 5 to 50 percent by weight propylene oxide and 50 to 85 percent by weight methanol. In a preferred embodiment of the present invention, the mixture (M) comprises from 5 to 15 percent by weight, preferably from 6 to 12 percent by weight and particularly preferably from 8 to 10.5 percent by weight of propylene oxide, and from 55 to 85 percent by weight, preferably from 60 to 80 percent by weight and particularly preferably from 65 to 75 percent by weight, of methanol.

With regard to the method of the present invention, mixture (M) may comprise one or more additional compounds. As to these compounds, no specific restrictions exist on the condition that propylene oxide can be distilled overhead from the extractive distillation column so as to separate propylene oxide from the methanol comprised in (M).

According to a preferred embodiment, the mixture (M) additionally comprises water, more preferably water in an amount of up to 25, more preferably from 1 to 25, more preferably from 2 to 25, more preferably from 3 to 25 percent by weight, more preferably from 4 to 25, more preferably from 5 to 25, more preferably from 6 to 25, more preferably from 7 to 25, more preferably from 8 to 25, more preferably from 9 to 25 and still more preferaby from 10 to 25 percent by weight of water, based on the total weight of mixture (M). Therefore, the mixture (M) for example may comprise from 10 to 25 or from 10 to 20 or from 10 to 15 or from 15 to 25 or from 15 to 20 or from 20 to 25 percent by weight water, based on the total weight of mixture (M).

According to a preferred embodiment where (M) comprises from 10 to 25 percent by weight of water, (M) preferably comprises from 5 to 45, more preferably from 5 to 40, more preferably from 5 to 35, more preferably from 5 to 30, more preferably from 5 to 25, more preferably from 5 to 20 and still more preferably from 5 to 15 percent by weight of propylene oxide, based on the total weight of mixture (M).

Therefore, the present invention also provides a method as described above wherein the mixture (M) comprises form 50 to 85 percent by weight methanol, from 5 to 15 percent by weight propylene oxide, and from 10 to 25 percent by weight water, based on the total weight of the mixture (M).

In addition to methanol and propylene oxide and, preferably, water, the mixture (M) may comprise at least one further compound.

According to a preferred embodiment of the present invention, the mixture (M) directly or indirectly results from a process where propylene oxide is prepared by reacting propene with a hydroperoxide in the presence of methanol as solvent. Therefore, the mixture (M) may additionally comprise unreacted propene and/or unreacted hydroperoxide and/or at least one by-product of said epoxidation reaction such as propylene glycol and/or acetaldehyde.

The reaction mixture obtained from said epoxidation reaction may be directly introduced in (i) as mixture (M) if the content of (M) regarding methanol, propylene oxide and preferably water is within above-mentioned ranges.

According to an especially preferred embodiment of the present invention, the reaction mixture obtained from said epoxidation reaction is worked up prior to the introduction in (i) of the inventive method. Working up the reaction mixture obtained from said epoxidation reaction may be carried out in each conceivable way on the condition that a mixture (M) is obtained which may be introduced in (i). Said work up may comprises the separation and/or the addition of at least one compound from and/or to the mixture obtained from the epoxidation reaction. Preferably, at least one compound is separated from the mixture obtained from the epoxidation reaction.

According to an even more preferred embodiment of the present invention, at least one compound is separated from the mixture obtained during work up from the epoxidation reaction, said at least one compound having a lower boiling point than propylene oxide, methanol and preferably water.

Depending on the reaction conditions applied and the reactants used for the epoxidation reaction, these low boilers may be, for example, unreacted propene and/or propane the latter being introduced, for example, in the epoxidation reaction in case, e.g., chemical grade propene is used as reactant having a volume ratio of propene:propane of from about 99.5:0.5 to 94:6.

According to a still further preferred embodiment of the present invention, unreacted propene is separated from the reaction mixture obtained from the epoxidation reaction in at least one distillation column, and the high boiling fraction whose respective content regarding methanol, proylene oxide and water are within the above-mentioned ranges is introduced as (M) in (i) of the method of the present invention.

Therefore, the present invention also provides a method of preparing propylene oxide, said reaction comprising reacting propene with a hydroperoxide in methanol as solvent, said reaction resulting in a mixture (M) comprising 5 to 15 percent by weight propylene oxide, 50 to 85 percent by weight methanol, and 10 to 25 percent by weight water, or preferably resulting in a mixture comprising propylene oxide, methanol, water, unreacted propene and optionally propane, said mixture being worked up to give said mixture (M) comprising 5 to 15 percent by weight propylene oxide, 50 to 85 percent by weight methanol, and 10 to 25 percent by weight water, and said mixture being further subjected to at least steps (i) to (iii) as described hereinabove and hereinunder. According to this embodiment of the present invention, working up preferably comprises separating propene and, if present, preferably also propane and/or acetaldehyde, by distillation so as to give a mixture (M), preferably comprising not more than 500 ppm, preferably not more than 400 ppm and especially preferably not more than 350 ppm of propene and comprising not more than 50 ppm, preferably not more than 25 ppm and especially preferably not more than 10 ppm of propane, and preferably not more than 200 ppm, more preferably not more than 150 ppm and especially preferably not more than 100 ppm of acetaldehyde. Accordingly, a mixture (M) is obtained comprising especially preferably not more than 350 ppm of propene and not more than 10 ppm of propane and not more than 100 ppm of acetaldehyde. According to a still further preferred embodiment of the present invention, the mixture (M) introduced in (i) comprises not more than 1 percent by weight, more preferably not more than 0.75 percent by weight and especially preferably not more than 0.65 percent by weight of high boiling compounds such as methoxypropanols and/or hydroperoxide.

In the context of the present invention, the term "hydroperoxide" refers to a compound of the formula ROOH. Details regarding the preparation of hydroperoxides and regarding hydroperoxides which can be used, inter alia, in the method of the present invention may be found in DE-A-198 35 907 the respective content of which is incorporated in the context of the present invention by reference. Examples of hydroperoxides which can be used for the purposes of the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethyinaphthalene hydroperoxide, peracids such as peracetic acid and hydrogen peroxide. Mixtures of two or more hydroperoxides can also be used according to the present invention. Preference is given to using hydrogen peroxide as hydroperoxide in the method of the present invention, and further preference is given to using an aqueous hydrogen peroxide solution. Most preferably, the aqueous hydrogen peroxide solution comprises hydrogen peroxide in a concentration in the range of from 1 to 90, more preferably of from 10 to 70 and especially preferably of from 30 to 50 wt.-%, based on the total weight of the solution. It is also possible to use a mixture of two or more different hydroperoxides.

The epoxidation reaction the mixture (M) directly or indirectly is obtained from may be carried out in the presence of each suitable catalyst or a suitable combination of two or more catalysts. Particularly preferred, a zeolite containing titanium is employed, wherein zeolites known to the person skilled in the art as "titanium silicalites" (TS) are particularly preferred. Such zeolites containing titanium, in particular those having a crystalline structure of the MFI-type as well as ways for producing them are described, for example, in WO 98/55228, EP-A-0 311 983, or EP-A-0 405 978. The respective content of these documents is hereby incorporated by reference. In addition to Si and Ti, said zeolite materials may contain additional elements, such as aluminum, zirconium, tin, iron, cobalt, nickel, gallium, boron, or small amounts of fluorine. It is possible that the titanium of the zeolite is partly or completely replaced by vanadium, zirconium, or niobium, or any mixture of two or more of these components. Zeolites containing titanium and having a MFI-structure are known to yield a characteristic pattern in X-ray diffraction. Furthermore, these materials display a vibration band in the infrared (IR) at approximately 960 $cm^{-1}$. Therefore, it is possible to distinguish the zeolites containing titanium from crystalline or amorphous $TiO_2$-phases or from alkaline metal titanates. In a further preferred embodiment, the at least one zeolite catalyst comprises at least one of the elements titanium, germanium, tellurium, vanadium, chromium, niobium, zirconium. Particularly preferred are zeolite catalysts having a pentasil zeolite structure, in particular the structural types that can be, via X-ray diffraction, assigned to the structure types of ABW-, ACO-, AEI-, AEL-, AEN-, AET-, AFG-, AFI-, AFN-, AFO-, AFR-, AFS-, AFT-, AFX-, AFY-, AHT-, ANA-, APC-, APD-, AST-, ATN-, ATO-, ATS-, ATT-, ATV-, AWO-, AWW-, BEA-, BIK-, BOG-, BPH-, BRE-, CAN-, CAS-, CFI-, CGF-, CGS-, CHA-, CHI-, CLO-, CON-, CZP-, DAC-, DDR-, DFO-, DFT-, DOH-, DON-, EAB-, EDI-, EMT-, EPI-, ERI-, ESV-, EUO-, FAU-, FER-, GIS-,-GME-, GOO-, HEU-, IFR-, ISV-, ITE-, JBW-, KFI-, LAU-, LEV-, LIO-, LOS-, LOV-, LTA-, LTL-, LTN-, MAZ-, MEI-, MEL-, MEP-, MER-, MFI-, MFS-, MON-, MOR-, MSO-, MTF-, MTN-, MTT-, MTW-, MWW-, NAT-, NES-, NON-, OFF-, OSI-, PAR-, PAU-, PHI-, RHO-, RON-, RSN-, RTE-, RTH-, RUT-, SAO-, SAT-, SBE-, SBS-, SBT-, SFF-, SGT-, SOD-, STF-, STI-, STT-, TER-, THO-, TON-, TSC-, VET-, VFI-, VNI-, VSV-, WIE-, WEN-, YUG-, ZON, as well as mixed structures of at least two or more of the aforementioned structures. Furthermore, it is conceivable to use zeolite catalysts containing titanium with the structure of ITQ-4, ITQ-9, SSZ-24, TTM-1, UTD-1, CIT-1 or CIT-5. Furthermore zeolites containing titanium are such of the structure types ZSM-48 or ZSM-12. Zeolites containing titanium of the structure MFI, MEL or MFI/MEL mixed structures, as well as MWW, BEA or mixed structures thereof are preferred in the context of the present invention. In the context of the present invention, zeolite catalysts containing titanium that are referred to, in general, as "TS-1", "TS-2" or "TS3", as well as zeolites containing titanium displaying a structure that is isomorphous to zeolite beta are further preferred.

Although it is possible to carry out the reaction using a suspension catalyst, particular preference is given to a heterogeneous catalyst and still more preferably a fixed-bed catalyst. Therefore, according to this preferred embodiment of the present invention, it is not necessary to separate the catalyst from the reaction mixture obtained from the epoxidation reaction.

Therefore, the present invention also provides a method of separating propylene oxide from a mixture (M) comprising propylene oxide, methanol and preferably water, as described above, wherein the mixture (M) is directly or indirectly, after at least one work up step, obtained from an epoxidation process wherein propene is reacted with a hydroperoxide, preferably hydrogen peroxide, in the presence of methanol as solvent and in the presence of a fixed-bed catalyst, preferably a fixed-bed zeolite catalyst, more preferably a fixed-bed titanium zeolite catalyst, still more preferably a fixed-bed TS-1 type titanium silicalite catalyst, and wherein said catalyst does not have to be separated from the reaction mixture resulting from the epoxidation process.

Accordingly, the present invention also provides a method of preparing propylene oxide, said reaction comprising reacting propene with a hydroperoxide, preferably hydrogen peroxide, in methanol as solvent, said reaction resulting in a mixture (M) comprising 5 to 15 percent by weight propylene oxide, 50 to 85 percent by weight methanol, and 10 to 25 percent by weight water, or preferably resulting in a mixture comprising propylene oxide, methanol, water, unreacted propene and optionally propane, said mixture being worked up to give said mixture (M) comprising 5 to 15 percent by weight propylene oxide, 50 to 85 percent by weight methanol, and 10 to 25 percent by weight water, and said mixture being further subjected to at least steps (i) to (iii) as described hereinabove and hereinunder, wherein the epoxidation is carried out in the presence of a fixed-bed catalyst, preferably a fixed-bed zeolite catalyst, more preferably a fixed-bed titanium zeolite catalyst, still more preferably a fixed-bed TS-1 type titanium silicalite catalyst, and wherein said catalyst does not have to be separated from the reaction mixture resulting from the epoxidation process.

In (i) of the present invention, any suitable extractive distillation column may be used. Preferably, the column has up to 80 theoretical plates such as from 10 to 80 or from 20 to 80 or from 30 to 80 or from 40 to 80 of from 50 to 80 or from 60 to 80 or preferably from more than 60 to 80 such as from 61 to 80 or from 65 to 80 or from 70 to 80 or from 75 to 80. Preferably, the column has more than 60 theoretical plates such as from 61 to 65 theoretical plates. Two or more columns may be used according to the present invention wherein two or more columns may be connected in series and/or two or more columns may be arranged in parallel. Preferably, one column is used.

According to (ii) of the present invention, at least one polar solvent is added. As to the chemical nature of the at least one polar solvent, no specific limitations exist on the condition that extractive distillation is possible under the conditions of (iii). Accordingly, no hydrocarbons, especially no C7-C9 hydrocarbons such as n-octane are used as extracting solvents, neither alone nor in combination with a polar solvent such as water.

Preferred polar solvents are water, alcohols having one or more hydroxy groups such as one, two, three or more hydroxy groups, preferably monools and diols, or ethers, preferably ether compounds having at least one hydroxy groups, preferably one hydroxy group such as 1-methoxy-2-propanol and/or 2-methoxy-1-propanol. Especially preferred is water wherein, for example, demineralized water, potable water, suitable industrial water, suitable waste water, especially suitably treated waste water, suitable process water or a mixture of two or more thereof can be used. The water introduced in the process of the present invention should be essentially free of organic material, especially essentially free of methanol. According to one embodiment of the present invention, the water introduced in (ii) is a process water from a suitable process such as a process carried out in the epoxidation plant in which the method of the present invention is conducted. According to one aspect of the present invention, the process water is taken from a process in the epoxidation plant where methanol as solvent of the epoxidation reaction and water are separated from each other as it is the case in step (v) described hereinunder. Preferably, the water is taken from the bottom of at least one distillation column in which methanol as solvent of the epoxidation reaction and water are separated. More preferably, the water resulting from said separation process, optionally after one or more additional purification steps, is introduced in (ii), and the methanol resulting from said separation process, optionally after one or more additional purification steps, is recirculated as solvent into the epoxidation reaction. Thus, the present invention also relates to a method as described above wherein an integrated process is implemented by working up a mixture comprising methanol and water by separating methanol and water from each other, and by recirculating the separated water, optionally after one or more additional purification steps, preferably without any additional purification steps, into (ii), and optionally recirculating the separated methanol, optionally after one or more additional purification steps, as solvent into the epoxidation reaction from which the mixture (M) introduced in (i) results.

Therefore, the present invention also provides a method of separating propylene oxide from a mixture (M) as described above wherein water is introduced as polar solvent into said extractive distillation column in (ii).

According to an even more preferred embodiment, no other solvent except water is introduced as polar solvent in (ii). According to another preferred embodiment, no propylene glycol is used as polar solvent.

The preferred embodiment according to which water and no propylene glycol is used as polar solvent, shows, among others, the advantages that water is cheaply available compared to propylene glycol and can be discarded without having disadvantageous ecological impacts. Therefore, in case propylene glycol is used as polar solvent, working up and recirculating the propylene glycol is necessary in order to render the process ecologically and economically efficient. However, working up necessarily includes at least one additional process step which is superfluous in case water is used as polar solvent.

According to a preferred embodiment of the present invention, the at least one polar solvent is introduced in the extractive distillation column about 15 theoretical plates, more preferably about 10 theoretical plates below the upper end of the extractive distillation column.

The at least one solvent, preferably water, may be introduced in the column as liquid or as vapor or as liquid as well as as vapor. If two or more solvents are used, at least one solvent may be introduced as liquid and at least one other solvent may be introduced as vapor.

According to a preferred embodiment, water is used as polar solvent and introduced in the extractive distillation column as liquid and/or as vapor, more preferably as vapor. Still more preferably, the vapor introduced in (ii) has a pressure to not more than 2 bar, more preferably of not more than 1 bar, more preferably not more than 900 mbar and especially preferably not more than 800 bar.

As far as the amount of polar solvent introduced in the extractive distillation column according to (ii) is concerned, no specific limitations exist. Preferably, polar solvent, in particular water, is introduced in an amount of not more than 2 percent by weight, based on the weight of the mixture (M). More preferably, the polar solvent is introduced in an amount of not more than 1.8, more preferably not more than 1.6, more preferably not more than 1.4, more preferably not more than 1.2 and still more preferably not more than 1 percent by weight, based on the weight of the mixture (M). Further preferred are amounts of polar solvent of at least 0.2, more preferably at least 0.25, more preferably at least 0.3 and still more preferably at least 0.4 percent by weight, based on the weight of the mixture (M). Therefore, preferred ranges are, for example, from 0.2 to 2, more preferably from 0.3 to 1.6, more preferably from 0.4 to 1.2, and still more preferably from 0.45 to 1 percent by weight, based on the weight of the mixture (M).

Therefore, the present invention also provides a method of separating propylene oxide from a mixture (M), as described above, wherein in (ii), at least one polar solvent, in particular water, preferably as vapor at a pressure of preferably not more than 2 bar, is introduced in an amount of from 0.45 to 1 percent by weight, based on the weight of the mixture (M).

Preferred mass ratios of propylene oxide comprised in (M): extracting solvent added in (ii) are from 0.6:1 to 70:1, more preferably from 1:1 to 20:1 and especially preferably from 3:1 to 8:1 such as, for example, from 4:1 to 7:1 or from 5:1 to 7:1 or from 6:1 to 7:1.

Distillation in (iii) is carried out at a bottoms temperature of from 40 to 70° C. at a pressure in the range of from 300 to 750 mbar. Other preferred ranges of the pressure at which distillation is carried out are from 300 to 700, more preferably from 300 to 650, more, preferably from 300 to 600, more preferably from 300 to 550 and still more preferably from 300 to 500 mbar, or from 350 to 750, more preferably from 400 to 750, more preferably from 450 to 750, more preferably from 450 to 700, more preferably from 450 to 650, more preferably from 450 to 600, more preferably from 450 to 550 and especially preferably from 450 to 500 mbar.

Therefore, the present invention also provides a method of separating propylene oxide from a mixture (M) as described above, wherein in (iii), distillation is carried out at a pressure of from 300 to 500 mbar, in particular from 450 to 500 mbar.

The term "pressure at which the distillation is carried out" as used in the context of the present invention relates to the pressure at the top of the column in which the distillation is carried out.

Especially preferred bottoms temperatures of the extractive distillation are for example from 40 to 70° C. or from 40 to 65° C. or from 40 to 60° C. or from 45 to 70° C. or from 45 to 65° C. or from 45 to 60° C. or from 50 to 70° C. or from 50 to 65° C. or from 50 to 60° C.

Especially preferred combinations of pressure ranges and bottoms temperature ranges are for example from 300 to 750 mbar and from 40 to 70° C. or from 300 to 500 mbar and from 40 to 60° C. or from 450 to 500 mbar and from 50 to 60° C.

Therefore, the present invention also provides a method of separating propylene oxide from a mixture (M) as described above, wherein in (iii), distillation is carried out at a pressure of from 300 to 500 mbar and at a temperature of from 40 to 60° C., more preferably at a pressure of from 450 to 500 mbar and at a temperature of from 50 to 60° C.

Therefore, the present invention provides a method of separating propylene oxide from a mixture (M) by extractive distillation, preferably using water as extracting solvent in an amount of not more than 2 percent by weight based on the weight of (M), wherein the extractive distillation is carried out at low pressures of 750 mbar and below, preferably from 300 to 750 mbar, more preferably from 300 to 500 mbar and especially preferably from 450 to 500 mbar, and simultaneously at low temperatures of 70° C. and below, preferably from 40 to 70° C., more preferably from 40 to 60° C. and still more preferably from 50 to 60° C. such as at about 51, 52, 53, 54, 55, 56, 57, 58 or 59° C.

As extractive distillation column, it is essentially possible to use any column. Particular preference is given to a distillation column configured as a packed column, more preferably a packed column containing ordered packing. Such a packed column has a high separation efficiency per meter of packing and displays only a very small pressure drop. While the ordered packing mentioned can essentially be of any type, preference is given to packing which has a specific surface area in the range from 100 to 750 $m^2/m^3$. It is possible to use sheet metal packing, for example from Montz (type B1 100 to B1 500) or from Sulzer ChemTech (Mellapak 125 to Mellapak 750), or mesh packing from Montz (type A3 500 to A3 750) or from Sulzer ChemTech (type BX or CY). The unit $m^2/m^3$ refers to the geometric surface area of the material forming the packing per cubic meter of packing.

According to the present invention, the propylene oxide fraction separated from methanol and water is preferably distilled overhead.

The propylene oxide fraction distilled overhead in (iii) preferably comprises at least 99.0, more preferably at least 99.5, more preferably at least 99.6, and still more preferably at least 99.7 percent by weight propylene oxide, based on the total weight of the propylene oxide fraction.

The propylene oxide fraction distilled overhead in (iii) preferably comprises not more than 500 ppm, more preferably not more than 200 ppm, more preferably not more than 100 ppm, more preferably not more than 50 ppm, more preferably not more than 20 ppm and still more preferably not more than 10 ppm of methanol, based on the total weight of the propylene oxide fraction.

The propylene oxide fraction distilled overhead in (iii) preferably comprises not more than 200 ppm, more preferably not more than 100 ppm, more preferably not more than 50 ppm, more preferably not more than 25 ppm, and still more preferably not more than 20 ppm of water, based on the total weight of the propylene oxide fraction.

The propylene oxide fraction distilled overhead in (iii) preferably comprises not more than 0.5, more preferably not more than 0.3, and still more preferably not more than 0.25 percent by weight of propene and propane, based on the total weight of the propylene oxide fraction.

At the extractive distillation conditions according to the present invention, the high boiler fraction at the bottom of the column comprises, in addition to water and methanol, not more than 100 ppm, preferably not more than 75 and especially preferably not more than 50 ppm of propylene oxide, based on the weight of the high boiler fraction, At the extractive distillation conditions according to the present invention where no propylene glycol but preferably water is used as extracting polar solvent in (ii), the high boiler fraction comprises, in addition to water and methanol, not more than 1, preferably not more than 0.5 and especially preferably not more than 0.2 percent by weight of propylene glycol, based on the weight of the high boiler fraction.

According to an especially preferred embodiment of the present invention, the propylene oxide fraction distilled overhead in (iii) is partially refluxed into the extractive distillation column. According to an even more preferred embodiment, the mass ratio of reflux:distillate is smaller than 5, more preferably smaller than or equal to 4.5 and especially preferably smaller than or equal to 4 such as about 3.5 or about 3.6 or about 3.7 or about 3.8 or about 3.9 or 4.

Therefore, the present invention also provides a method of separating propylene oxide from a mixture (M) as described above, wherein the distillate obtained overhead from (iii) is partially refluxed into said extractive distillation column and wherein the ratio of reflux to distillate is smaller than or equal to 4.

Thus, the extractive distillation process of the present invention combines the advantages of low distillation pressures, low distillation temperatures and, simultaneously, a low reflux:distillate ratio.

The propylene oxide fraction distilled overhead may be used as such or subjected to at least one further work up step in case the content of this fraction with regard to compounds such as propene, propane, and/or acetaldehyde is too high for the purpose the propylene oxide is meant for. Such a work up may comprise, for example, a fractional distillation where low boilers are withdrawn overhead and a purified propylene oxide fraction is withdrawn as bottoms stream or as side stream. Subsequently, if necessary, this bottoms stream may be subjected to at least one additional purification process.

The bottoms stream withdrawn from the extractive distillation column in (iii) may be used as such or after at least one work up step in at least one other process or may be recirculated in the method of the present invention. According to a preferred embodiment of the present invention, the bottoms stream is worked up in one, two or more steps to give a mixture comprising at least 97 percent by weight of methanol, not more than 2 percent by weight of water, and not more than 50 ppm of acetaldehyde, based on the total weight of said mixture, and the methanol thus purified is recirculated in the method of the present invention, preferably as solvent for the epoxidation reaction the mixture (M) results from.

Depending on the polar solvent used in (ii) as extracting solvent, this solvent may be suitably separated from the bottoms stream and recirculated in the method of the present invention, preferably as polar solvent in (ii), A further advantage of the preferred method of the present invention according to which water is used as polar solvent, working up the bottoms stream obtained in (iii) so as to obtain the purified polar solvent to be recirculated in (ii) is not necessary since water is cheaply available, contrary to, e.g., propylene glycol described in U.S. Pat. No. 5,849,938 as preferred extracting solvent.

Accordingly, the present invention provides a method of preparing propylene oxide, said reaction comprising reacting propene with a hydroperoxide, preferably hydrogen peroxide, in methanol as solvent and preferably in the presence of a fixed-bed titanium silicalite catalyst, said reaction resulting in a mixture comprising propylene oxide, methanol, water, unreacted propene and optionally propane, said mixture being worked up to essentially completely remove unreacted propene, to give a mixture (M) comprising 15 percent by weight propylene oxide, 50 to 85 percent by weight methanol, and 10 to 25 percent by weight water, said method further comprising (i) introducing said mixture (M) into an extractive distillation column;

(ii) additionally introducing a polar solvent, preferably water, more preferably water as vapor, wherein the vapor is introduced at a pressure of not more than 2 bar, preferably not more than 1 bar, more preferably not more than 900 mbar and especially preferably not more than 800 mbar, into said extractive distillation column in an amount of not more than 2, preferably from 0.45 to 1 percent by weight of the mixture (M);

(iii) distilling propylene oxide overhead from said extractive distillation as top stream at a pressure of from 300 to 750, more preferably from 300 to 500, especially preferably from 450 to 500 mbar and a bottoms temperature of from 40 to 70° C., preferably from 40 to 60° C. and especially preferably from 50 to 60° C.;

(iv) withdrawing a bottoms stream from said extractive distillation column, said bottoms stream comprising 100 ppm propylene oxide or less, preferably 75 ppm propylene oxide or less, especially preferably 50 ppm propylene oxide or less, based on the total weight of the bottoms stream, and withdrawing a top stream from said distillation column, said top stream comprising 500 ppm methanol or less, preferably 200 ppm methanol or less, more preferably 100 ppm methanol or less, more preferably 50 ppm methanol or less, more preferably 20 ppm methanol or less and especially preferably 10 ppm methanol or less, based on the total weight of the top stream, and (v) optionally at least partially recirculating the methanol comprised in the bottoms stream of (iv) as solvent into the reaction where the propene is reacted with the hydroperoxide.

The following examples and figures are used to illustrate the present invention and are not meant to be limiting.

DETAILED DESCRIPTION OF THE FIGURES

FIG. 1 shows a preferred embodiment according to the invention. A mixture (M) and an extracting solvent (1) are introduced into an extractive distillation column (K200) (steps (i) and (ii)). Propylene oxide is distilled overhead from (K200) as top stream (step (iii)). A heat exchanger (W230) is used to condense the top stream of the extractive distillation column (K200). As cooling agent (3) used in the heat exchanger (W230), chilled water and cooling water, respectively, is employed. To heat the reboiler of the column (K200), a heat exchanger (W200) is employed, and low pressure steam (2) is used as heating source. Heat exchanger (W220) is used to preheat mixture (M) before it is introduced into the column (K200).

Figure 2:
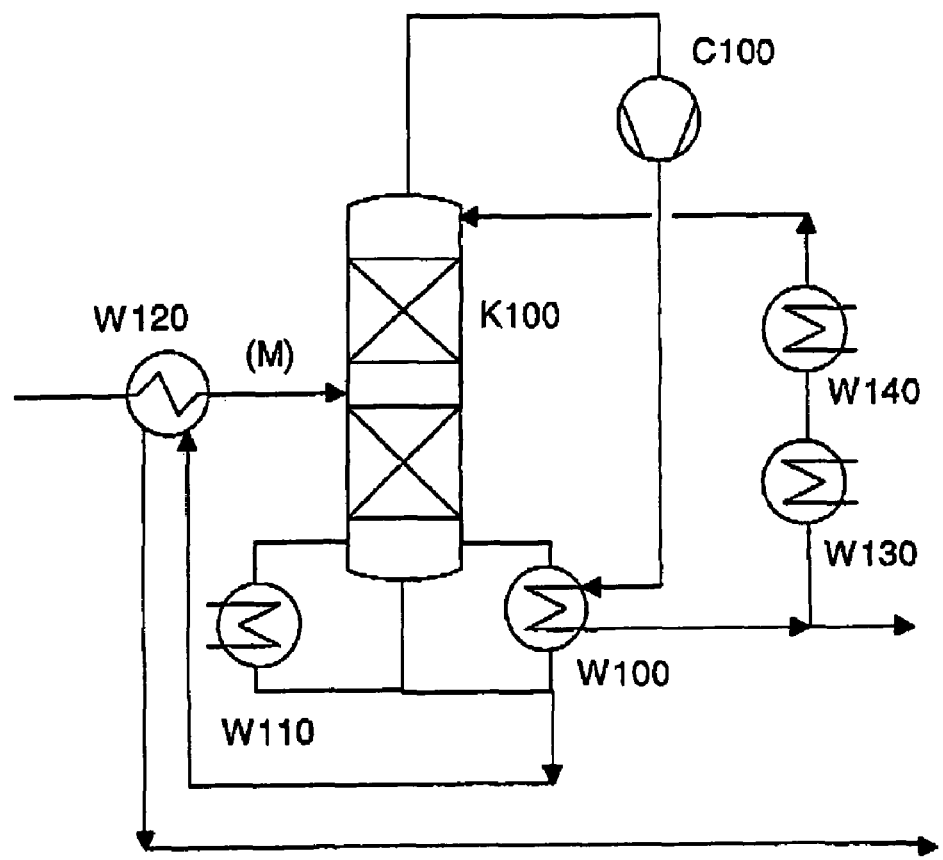

FIG. 2 shows an embodiment where no polar solvent is used for the distillation. A mixture (M) is introduced into a distillation column (K100). Propylene oxide is distilled overhead from (K100) as top stream which is compressed in an electric compressor (C100), and the compressed vapor stream is condensed in a heat exchanger (W100) where at least part of the heat of condensation is transferred to a reboiler employed in the extractive distillation column (K100). The heat exchanger (W110) as shown in FIG. 2 is only used for starting the distillation process, i.e., during a continuous distillation process this heat exchanger (W110) is not used. The cooled and condensed stream leaving the heat exchanger (W100) is then divided, and a part of the stream is passed to a first heat exchanger (W130). The cooled stream leaving heat exchanger (W130) is then passed to a second heat exchanger (W140) where the stream is cooled further and ultimately recirculated as reflux on the top of the column (K100). If necessary and/or desired, part of the energy stored in the bottom stream of the distillation column may be used in a further heat exchanger (W120) where the mixture (M) is heated or preheated before it is introduced into-column (K100).

Figure 3:
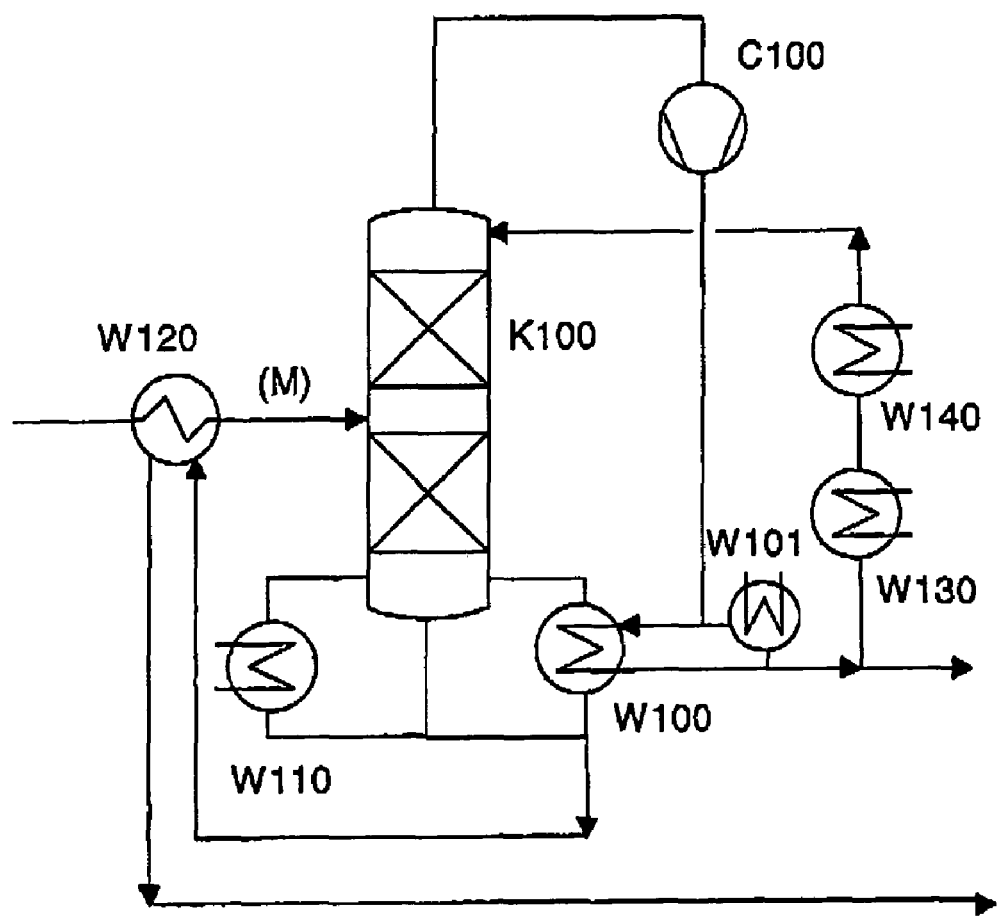

FIG. 3 shows another embodiment where no polar solvent is used for the distillation. In contrast to the process depicted in FIG. 2, the process according to FIG. 3 encompasses a further heat exchanger (W101). Depending on the amount of energy which shall be withdrawn from the compressed vapor stream and be transferred to a reboiler employed in the distillation column (K100), it might be necessary to divide the compressed vapor stream, and pass one part of the stream to heat exchanger (W100) and one part to heat exchanger (W101).

EXAMPLES

A stream, the outlet of an epoxidation unit from which nearly all light boiling components were separated off, is subjected to different PO/MeOH separation units (examples 1 to 3). In all examples, this stream has the composition according to table 1:

TABLE 1

| composition of stream | |
|---|---|
| stream | mass % |
| propylene | 0.013423 |
| formaldehyde | 0.011839 |
| acetaldehyde | 0.026834 |
| propylene oxide | 9.446765 |

TABLE 1-continued

| composition of stream | |
|---|---|
| stream | mass % |
| methanol | 71.97108 |
| water | 17.54493 |
| glycol ethers | 0.43074 |
| propylene glycol | 0.051477 |
| others (heavy boilers) | up to 100 |

Example 1

Extractive Distillation In Vacuo with Water

The process of example 1 is carried out in a unit of appartuses as shown in FIG. 1. In FIG. 1, a heat exchanger (W230) is shown in which the top stream of an extractive distillation column (K200) is cooled using chilled water and cooling water, respectively. To heat the reboiler of the column, a heat exchanger (W200) is employed, and low pressure steam (2) is used as heating source. Heat exchanger (W220) is used to preheat mixture (M), i.e. the feed according to table 1, before it is introduced into the column (K200).

The above described stream (table 1) is fed to an extractive distillation tower (K200) containing 80 theoretical stages. Low pressure steam (2) is used to heat the reboiler of the column via heat exchanger (W200). The condenser (W230) is operated with chilled water (3), which is prepared in a chilled water unit (not shown in FIG. 1). The column (K200) is operated in vacuo at 500 mbar, and water is used as extracting solvent (1). The feeding point are as follows: feed stream of the column is fed on stage 45 from the top of the column, water as extracting agent is fed on stage 12 from the top of the column, at a flow rate of 5.2% with respect to the propylene oxide contained in the feed stream. Purified propylene oxide is taken at the top of the tower. The tower is operated at a mass reflux ratio (reflux:distillate) of 3.9. The top propylene oxide stream contains, beside the light boilers, 10 ppm of MeOH and 55 ppm of water. The bottom stream contains 50 ppm of propylene oxide, MeOH, water and all other heavy boilers.

Example 2

Extractive Distillation with (a) Water and (b) Propylene Glycol at 2 Bar (Comparative Examples)

The processes of example 2 are carried out in a unit of appartuses as shown in FIG. 1. In FIG. 1, a heat exchanger (W230) is shown in which the top stream of an extractive distillation column (K200) is cooled using chilled water and cooling water, respectively, To heat the reboiler of the column, a heat exchanger (W200) is employed, and low pressure steam (2) is used as heating source. Heat exchanger (W220) is used to pre-heat mixture (M), i.e. the feed according to table 1, before it is introduced into the column (K200).

(a) The above described stream (table 1) is fed to an extractive distillation tower (K200) containing 80 theoretical stages. The column (K200) is operated at a pressure of 2 bar. Water is used as extracting solvent (1). Low pressure steam is used as an external heating source to heat the reboiler of the column. The condenser (W230) is operated with cooling tower water. The reboiler duty is 31.5 MW, the condenser duty 30.2 MW. The feeding points are as follows: the feed stream of the column is fed on stage 50 from the top of the column, water as extracting agent is fed on stage 12 from the top of the column, at a flow rate of 10.4% with respect to the propylene oxide contained in the feed stream. The tower is operated at a mass reflux ratio (reflux:distillate) of 6.1. Purified propylene oxide is taken at the top of the tower. The top propylene oxide stream contains, beside the light boilers, 10 ppm of MeOH and 1,500 ppm of water. The bottom stream contains 50 ppm of propylene oxide, MeOH, water and all other heavy boilers.

b) The above described stream (table 1) is fed to an extractive distillation tower (K200) containing 80 theoretical stages. The column (K200) is operated at a pressure 2 bar. Propylene glycol is used as extracting solvent (1). Low pressure steam is used as an external heating source to heat the reboiler of the column. The condenser (W230) is operated with cooling tower water. The reboiler duty is 36.5 MW, the condenser duty 34.5 MW. The feedings point are as follows the feed stream of the column is fed on stage 60 from the top of the column, propylene glycol as extracting solvent is fed on stage 2 from the top of the column, at a flow rate of 30% with respect to the propylene oxide contained in the feed stream. The tower is operated at a mass reflux ration (reflux:distillate) of 7.3. Purified propylene oxide is taken at the top of the tower. The top propylene oxide stream contains, beside the light boilers, 10 ppm of MeOH, The bottom stream contains 50 ppm of propylene oxide, MeOH, water, the added propylene glycol and all other heavy boilers.

Example 3

Fractional Distillation without Polar Solvent Including Compressing Top Stream of Distillation Column (Comparative Example)

The process of example 3 is carried out in a unit of appartuses as shown in FIG. 3.

The above described stream (table 1) is fed to a distillation tower (K100) containing 80 theoretical stages, equipped with a compressor (C100) to compress the top vapour outlet stream of the top of column. This stream is used as a heating source for the re-boiler of the distillation column. The column is operated in vacuo at 500 mbar. No extracting solvent is used. The feeding point of the feed stream is on stage 68 from the top of the column. Purified propylene oxide is taken at the top of the tower. The tower is operated at a mass reflux ratio (reflux:distillate) of 9.4. The reboiler duty is 49.5 MW. The top propylene oxide stream contains beside the lights 10 ppm of MeOH. The bottom stream contains 50 ppm of propylene oxide, MeOH, water and al the other heavies.

The following table 2 gives an overview of the described examples:

TABLE 2 overview of the described examples.

| | example | | | |
|---|---|---|---|---|
| | 1 | 2a | 2b | 3 |
| extracting solvent | water | water | prop. glycol | — |
| top pressure [bar] | 0.5 | 2 | 2 | 0.5 |
| top temperature [° C.] | 16.1 | 54.8 | 54.8 | 16.1 |

TABLE 2-continued overview of the described examples.

| | example | | | |
|---|---|---|---|---|
| | 1 | 2a | 2b | 3 |
| compression of top vapor stream | no | no | no | yes |
| theoretical stages | 80 | 80 | 80 | 80 |
| feeding point (from top) | 45 | 50 | 62 | 68 |
| feeding point extracting solvent (from top) | 12 | 12 | 2 | — |
| mass ratio extr. solvent/propylene oxide [%] | 5.2 | 10.4 | 30 | — |
| mass reflux ratio | 3.9 | 6.1 | 7.3 | 9.4 |
| bottom temperature of (K100/200) [° C.] | 55.9 | 89.5 | 91.5 | 55.8 |
| propylene oxide traces in bottom stream [ppm] | 50 | 50 | 50 | 50 |
| MeOH traces in distillate stream [ppm] | 10 | 10 | 10 | 10 |
| reboiler duty [MW] of (K100) or (K200) | 22 | 31.5 | 36.5 | 49.5 |
| electr. condenser energy consumption [MW] (C100) | — | — | — | 14.5 |
| condenser capacity cooling tower water [MW] (W230) | — | 30.2 | 34.5 | — |
| condenser capacity chilled water [MW] (W230) | 21.1 | — | — | — |
| cooling tower water [MW] (W130) | — | — | — | 6.0 |
| chilled water [MW] (W140) | — | — | — | 3.6 |
| heating source reboiler (K100/200) | low pressure steam | low pressure steam | low pressure steam | compr. top stream vapor |

We claim:

1. A method of separating propylene oxide from a mixture (M) comprising 5 to 15 percent by weight propylene oxide, 50 to 85 percent by weight methanol and 10 to 25 percent by weight water, said method comprising
   (i) introducing said mixture (M) into an extractive distillation column;
   (ii) additionally introducing a polar solvent into said extractive distillation column, wherein the polar solvent is introduced in an amount of 2% by weight of the mixture (M) or less;
   (iii) distilling propylene oxide overhead from said extractive distillation column at a bottoms temperature of from 40 to 70° C. and at a pressure of from 300 to 750 mbar.

2. The method as claimed in claim 1, wherein in (iii), propylene oxide is distilled overhead at a pressure of from 300 to 500 mbar.

3. The method as claimed in claim 1, wherein the polar solvent is introduced in an amount of from 0.45 to 1 percent by weight of the mixture (M).

4. The method as claimed in claim 1, wherein said extractive distillation column has up to 80 theoretical plates.

5. The method as claimed in claim 1, wherein water is used as polar solvent.

6. The method as claimed in claim 5, wherein the water is introduced as vapor at a pressure of not more than 2 bar.

7. The method as claimed in claim 1, wherein the distillate obtained overhead from (iii) is partially refluxed into said extractive distillation column and wherein the ratio of reflux to distillate is smaller than or equal to 4.

8. The method as claimed in claim 1, wherein the top stream distilled overhead comprises 100 ppm methanol or less.

9. The method as claimed in claim 1, wherein the bottoms stream withdrawn from said extractive distillation column has a propylene oxide content of 100 ppm or less.

10. The method as claimed in claim 1, wherein the mixture (M) is formed by reacting propene with hydrogen peroxide in methanol as solvent and in the presence of a titanium zeolite fixed-bed catalyst.

11. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column;
  (ii) additionally introducing water into said extractive distillation column in an amount of 2 percent by weight of the mixture (M) or less;
  (iii) distilling propylene oxide overhead from said extractive distillation colunm at a bottoms temperature of from 40 to 70° C. and at a pressure of from 300 to 750 mbar.

12. The method as claimed in claim 11, wherein in (iii), propylene oxide is distilled overhead at a pressure of from 300 to 500 mbar.

13. The method as claimed in claim 11, wherein the distillate obtained overhead from (iii) is partially refluxed into said extractive distillation column and wherein the ratio of reflux to distillate is smaller than or equal to 4.

14. The method as claimed in claim 11, wherein the top stream distilled overhead from said extractive distillation colunm comprises 100 ppm methanol or less and the bottoms stream withdrawn from said extractive distillation column has a propylene oxide content of 100 ppm or less.

15. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column;
  (ii) additionally introducing water into said extractive distillation in an amount of 2% by weight of the mixture (M) or less;
  (iii) distilling propylene oxide overhead from said extractive distillation column at a bottoms temperature of from 40 to 70° C. and at a pressure of from 300 to 750 mbar;
  wherein the distillate is partially refluxed into said extractive distillation column and wherein the mass ratio of reflux to distillate is smaller than or equal to 4.

16. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column;
  (ii) additionally introducing water into said extractive distillation in an amount of 2% by weight of the mixture (M) or less;
  (iii) distilling propylene oxide overhead from said extractive distillation column at a bottoms temperature of from 40 to 70° C. and at a pressure of from 300 to 750 mbar;
  (iv) withdrawing a bottoms stream from said extractive distillation column, said bottoms stream comprising 100 ppm propylene oxide or less, and with-drawing a top stream from said extractive distillation column, said top stream comprising 100 ppm methanol or less.

17. The method as claimed in claim 16, wherein the top stream distilled overhead in (iii) comprises 10 ppm methanol or less.

18. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column;
  (ii) additionally introducing water as vapor at a pressure of not more than 2 bar into said extractive distillation column in an amount of 2% by weight of the mixture (M) or less;
  (iii) distilling propylene oxide overhead from said extractive distillation column at a bottoms temperature of from 40 to 70° C. and a pressure of from 300 to 750 mbar.

19. The method as claimed in claim 18, wherein, in (ii), water is introduced into said extractive distillation column in an amount of from 0.45 to 1 percent by weight of the mixture (M) at a pressure of not more than 800 mbar.

20. The method as claimed in claim 18, wherein in (iii), propylene oxide is distilled overhead from said extractive distillation column at a bottoms temperature of from 40 to 60° C. and a pressure of from 300 to 500 mbar.

21. The method as claimed in claim 18, additionally comprising
  (iv) withdrawing a bottoms stream from said extractive distillation column, said bottoms stream comprising 100 ppm propylene oxide or less, and with-drawing a top stream from said extractive distillation column, said top stream comprising 100 ppm methanol or less.

22. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column;
  (ii) additionally introducing water into said extractive distillation column in an amount of 2 percent by weight of the mixture (M) or less;
  (iii) distilling propylene oxide overhead from said extractive distillation column at a bottoms temperature of from 40 to 60° C. and a pressure of from 300 to 500 mbar;
  (iv) withdrawing a bottoms stream from said extractive distillation column, said bottoms stream comprising 100 ppm propylene oxide or less, and with-drawing a top stream from said extractive distillation column, said top stream comprising 10 ppm methanol or less.

23. The method as claimed in claim 22, wherein in (iii), propylene oxide is distilled overhead at a pressure of from 450 to 500 mbar.

24. The method as claimed in claim 22, wherein in (iii), propylene oxide is distilled overhead at a temperature of from 50 to 60° C.

25. A method of preparing propylene oxide, said reaction comprising reacting propene with a hydroperoxide in methanol as solvent, said reaction resulting in a mixture (M) comprising 5 to 15 percent by weight propylene oxide, 50 to 85 percent by weight methanol, and 10 to 25 percent by weight water, or resulting in a mixture being worked up to give said mixture (M), said method further comprising (i) introducing said mixture (M) into an extractive distillation column;

(ii) additionally introducing water as steam at a pressure of not more than 900 mbar into said extractive distillation column in an amount of 0.45 to 1 percent by weight of the mixture (M);

(iii) distilling propylene oxide overhead from said extractive distillation as top stream at a pressure of from 450 to 500 mbar and a bottoms temperature of from 50 to 60° C.;

(iv) withdrawing a bottoms stream from said extractive distillation column, said bottoms stream comprising 100 ppm propylene oxide or less, and with-drawing a top stream from said extractive distillation column, said top stream comprising 50 ppm methanol or less.

26. The method as claimed in claim 25, wherein the hydroperoxide is hydrogen peroxide.

27. The method as claimed in claim 25, wherein the reaction of propene with a hydroperoxide in methanol as solvent is carried out in the presence of a fixed-bed titanium silicalite catalyst.

\* \* \* \* \*